US008022264B2

(12) United States Patent
Hatscher et al.

(10) Patent No.: US 8,022,264 B2
(45) Date of Patent: Sep. 20, 2011

(54) ADSORPTION COMPOSITION AND METHOD OF REMOVING CO FROM STREAMS

(75) Inventors: Stephan Hatscher, Syke (DE); Michael Hesse, Worms (DE)

(73) Assignee: BASF SE, Ludwigshafen (DE)

( * ) Notice: Subject to any disclaimer, the term of this patent is extended or adjusted under 35 U.S.C. 154(b) by 414 days.

(21) Appl. No.: 12/305,450

(22) PCT Filed: Jun. 15, 2007

(86) PCT No.: PCT/EP2007/055938
§ 371 (c)(1),
(2), (4) Date: Dec. 18, 2008

(87) PCT Pub. No.: WO2007/147783
PCT Pub. Date: Dec. 27, 2007

(65) Prior Publication Data
US 2009/0281365 A1 Nov. 12, 2009

(30) Foreign Application Priority Data

Jun. 21, 2006 (EP) .................................... 06115823

(51) Int. Cl.
*C07C 7/12* (2006.01)
(52) U.S. Cl. .................... 585/823; 585/820; 585/824
(58) Field of Classification Search .................. None
See application file for complete search history.

(56) References Cited

U.S. PATENT DOCUMENTS

| | | |
|---|---|---|
| 3,549,719 A | 12/1970 | Duyverman et al. |
| 3,676,516 A | 7/1972 | Haskell et al. |
| 4,552,861 A | 11/1985 | Courty et al. |
| 4,593,148 A | 6/1986 | Johnson et al. |
| 4,713,090 A | 12/1987 | Yokoe et al. |
| 4,835,132 A | 5/1989 | Sambrook |
| 4,871,710 A | 10/1989 | Denny et al. |
| 4,917,711 A | 4/1990 | Xie et al. |
| 5,328,672 A | 7/1994 | Montreuil et al. |
| 5,589,151 A | 12/1996 | Gary |
| 5,648,548 A | 7/1997 | Takaya et al. |
| 5,685,172 A | 11/1997 | Darredeau et al. |
| 5,891,220 A | 4/1999 | Gary |
| 6,238,640 B1 | 5/2001 | Eguchi et al. |
| 6,524,996 B1 | 2/2003 | Bender et al. |
| 6,723,295 B1 | 4/2004 | Baier et al. |
| 7,314,965 B2 | 1/2008 | Vorberg et al. |
| 2005/0241478 A1 | 11/2005 | Junicke et al. |

FOREIGN PATENT DOCUMENTS

| | | |
|---|---|---|
| CA | 2045060 | 1/1992 |
| DD | 153761 | 2/1982 |
| DE | 1929977 | 12/1969 |
| DE | 4021230 | 1/1991 |
| DE | 19848595 | 4/2000 |
| DE | 19950325 | 4/2001 |
| DE | 19963441 | 7/2001 |
| DE | 10241529 | 3/2004 |
| DE | 102005061322 | 6/2007 |
| EP | 296734 | 12/1988 |
| EP | 434062 | 6/1991 |
| EP | 537628 | 4/1993 |
| EP | 662595 | 7/1995 |
| EP | 691157 | 1/1996 |
| EP | 750933 | 1/1997 |
| EP | 804959 | 11/1997 |
| EP | 820960 | 1/1998 |
| JP | 55003856 | 1/1980 |
| JP | 02144125 | 6/1990 |
| JP | 05337363 | 12/1993 |
| WO | WO-9521146 | 8/1995 |
| WO | WO-9523644 | 9/1995 |
| WO | WO-9614280 | 5/1996 |
| WO | WO-9841597 | 9/1998 |
| WO | WO-0107383 | 2/2001 |
| WO | WO-0226619 | 4/2002 |
| WO | WO-02068119 | 9/2002 |
| WO | WO-02094435 | 11/2002 |
| WO | WO-03002252 | 1/2003 |
| WO | WO-03051493 | 6/2003 |
| WO | WO-2004022223 | 3/2004 |
| WO | WO-2004080589 | 9/2004 |
| WO | WO-2007093526 | 8/2007 |

OTHER PUBLICATIONS

International Preliminary Report on Patentability issued in International Application PCT/EP2007/055938 on Jan. 13, 2009.
Jung Bong Ko et al., "Cu-ZrO$_2$ catalysts for water-gas-shift reaction at low temperatures", Catalysis Letters, vol. 105, No. 3-4, 2005, pp. 157-161.
Wei Liu et al., "Total Oxidation of Carbon Monoxide and Methane over Transition Metal-Fluorite Oxide Composite Catalysts", Journal of Catalysis, vol. 153, 1995, pp. 304-316.
Huang et al., "CO oxidation over Cu, Cu$_2$O, and CuO", Catalysis Letters, vol. 87, 2003, pp. 173-178.

*Primary Examiner* — Tam M Nguyen
(74) *Attorney, Agent, or Firm* — Connolly Bove Lodge & Hutz LLP

(57) ABSTRACT

Carbon monoxide is removed from streams by adsorption on an adsorption composition which comprises copper and zirconium oxides but no zinc oxide, which comprises from 70 to 99.8% by weight of copper oxide and from 0.2 to 30% by weight of zirconium oxide, based on the total amount of the adsorption composition.

5 Claims, No Drawings

ADSORPTION COMPOSITION AND METHOD OF REMOVING CO FROM STREAMS

CROSS REFERENCE TO RELATED APPLICATIONS

This application is a National Stage of PCT/EP2007/055938 filed Jun. 15, 2007 which in turn claims priority from European Application 06115823.4 filed Jun. 21, 2006, the entire contents of which are incorporated herein by reference.

The present invention relates to an adsorption composition and a method of removing carbon monoxide (CO) from streams. In particular, the invention relates to an adsorption composition and a process for removing carbon monoxide from hydrocarbon streams.

In various fields of industry, it is important to have particularly pure streams available. In this context, "pure" means that the stream is free of constituents which would interfere in the intended use of the stream. An example is air for breathing, which has to be free of toxic compounds. Likewise, pure streams are required in, for instance, the production of electronic components in order to prevent introduction of contaminants which adversely affect the electronic properties of the components produced; among other things, particularly pure nitrogen or particularly pure argon is often required here as protective gas. Another example is provided by catalytic chemical reactions. Catalysts are often very sensitive to poisoning. Since, for economic reasons, the amount of feed stream used per volume or mass of catalyst is usually maximized, even extraordinarily small amounts of impurities in the feed stream can accumulate on the catalyst and poison it. In the case of olefin polymerization reactions of modern catalysts, for example metallocene catalysts, olefin streams which comprise no more than a few ppb of impurities (parts per billion, i.e. $10^{-9}$ parts of impurities per part of the desired substance) ("polymer grade" olefins) are typically required. Olefins from typical olefin sources (steam crackers, fluid catalytic crackers, dehydrogenations, MTO ("methanol to olefins") processes) usually comprise very much higher proportions (ppm or even parts per thousand range) of impurities such as carbon monoxide or oxygen ("chemical grade"); these proportions have to be reduced appropriately before use for polymerization.

The streams to be purified are typically air, nitrogen or argon or hydrocarbons such as ethylene, propylene, 1-butene, 2-butene, 1,3-butadiene or styrene. Typical impurities which generally have to be removed are oxygen and carbon monoxide and often also water, carbon dioxide, hydrogen or else sulfur compounds, arsenic compounds or antimony compounds. Methods of removing such impurities from streams are known.

Best known is the removal of carbon monoxide from oxygen-comprising gas streams, for example air for breathing. This is usually achieved by catalytic reaction of carbon monoxide with oxygen, generally over copper-comprising catalysts. The most-used catalyst for this reaction is hopcalite, a copper-manganese mixed oxide which is highly active for the reaction of carbon monoxide with oxygen and over which the highly toxic carbon monoxide reacts with oxygen to form carbon dioxide and which was originally developed for removal of CO from air in breathing masks.

However, other uses of hopcalite and methods of purifying streams other than air for breathing are also known. Thus, WO 98/041 597 A1 discloses a method of removing alkynes, singly or multiply unsaturated hydrocarbons, sulfur compounds, antimony compounds or arsenic compounds, oxygen, hydrogen and carbon monoxide from streams by means of a sequence of two or three particular catalytic and absorptive process steps. EP 662 595 A1 teaches a method of removing hydrogen, carbon monoxide and oxygen from cold liquid nitrogen by bringing it into contact with particular zeolites or other metal oxides, in particular hopcalite. EP 750 933 A1 discloses a similar method of removing oxygen and carbon monoxide from cold nitrogen or cold noble gases by bringing it/them into contact with metal oxides, in particular hopcalite. However, at the low temperatures of less than −40° C. which are employed, no or very little catalytic reaction takes place; oxygen and carbon monoxide are adsorbed on the hopcalite and react only at higher temperature, unless they are removed at low temperature in a desorption step. EP 820 960 A1 discloses a method of removing oxygen and carbon monoxide from nitrogen or noble gases by bringing it/them into contact with metal oxides such as hopcalite, in particular at temperatures of from 5 to 50° C.

T.-J Huang and D.-H. Tsai, Catalysis Letters 87 (2003) 173-178, report studies on the influence of the degree of oxidation of copper on the oxidation of carbon monoxide. $Cu_2O$ is overall more active than CuO, which is attributed to the higher mobility of oxygen in $Cu_2O$, compared to Cu or CuO.

WO 02/094 435 A1 teaches a method of removing CO oxidatively from ethylene at temperatures in the range from 70 to 110° C. over catalysts comprising copper and zinc.

WO 02/026 619 A2 discloses a method of removing carbon monoxide by means of the water gas shift reaction and WO 03/051 493 A2 discloses a method of selectively oxidizing carbon monoxide, in particular in gas streams comprising carbon monoxide, oxygen and hydrogen, in particular in fuel cells, and over catalysts comprising copper, a metal of the platinum group and a reducible metal on an oxidic support comprising activated aluminum, zirconium dioxide, titanium dioxide, silicon dioxide, zeolites or combinations thereof. The reducible metal oxide is selected from the group consisting of the oxides of Cr, V, Mo, Ce, Pr, Nd, Ti, Ni, Mn, Co and combinations thereof. U.S. Pat. No. 6,238,640 B1 describes a method of removing carbon monoxide from hydrogen-comprising gas streams by reaction with steam and oxygen to form carbon dioxide and hydrogen in the presence of a catalyst comprising copper oxide and aluminum oxide and also at least one metal oxide from the group consisting of zinc oxide, chromium oxide and magnesium oxide.

In these methods of removing carbon monoxide in the presence of oxygen, the reaction forms carbon dioxide. In subsequent processes, this can be inert or can itself be an interfering impurity. In the latter case, it is removed, and various methods of achieving this are also known. For example, CA 2 045 060 A1 teaches a method of removing carbon monoxide, carbon dioxide, hydrogen, oxygen and water vapor from inert gas streams at a temperature in the range from −30° C. to +40° C., in particular from −30° C. to 0° C., with carbon monoxide being reacted over transition metal oxides such as hopcalite or copper-cobalt oxide to form carbon dioxide and the latter being removed by adsorption on copper on an aluminum oxide support or nickel on an aluminum oxide or silicon dioxide support.

However, in some applications, carbon monoxide has to be removed by a method other than reaction with oxygen or water, for example when carbon monoxide but no oxygen, no water or only a substoichiometric amount thereof is comprised in the stream to be purified. In some applications, oxygen has to be removed before the carbon monoxide, particularly when not only carbon dioxide but also other interfering by-products can be formed. For example, oxidation products of a hydrocarbon (known as "oxygenates") can be formed in the removal of oxygen and carbon monoxide from liquid hydrocarbons such as propylene, butene, butadiene or styrene over copper-comprising catalysts and are themselves interfering impurities. In such cases, the oxygen has to be removed before removal of the carbon monoxide, and carbon monoxide cannot be removed by oxidation.

In such cases, carbon monoxide is therefore usually removed by distillation, but removal of CO down to residual contents in the ppb range is not possible in this way. However, adsorptive methods and adsorbents are also known for purifying streams. DE-A 1 929 977 teaches catalysts comprising from 20 to 60 parts of CuO on 100 parts of ZnO and their use for removing CO from ethylene and propylene streams at a temperature in the range from 50 to 200° C. U.S. Pat. No. 3,676,516 teaches a supported Cu catalyst in which from 20 to 95% of the copper is present as $Cu^{2+}$ and its use for removing CO from ethylene or propylene streams at a temperature below about 200° C., in the examples actually about 93° C. U.S. Pat. No. 4,917,711 discloses an adsorbent which comprises a copper compound on a high-surface-area support but also adsorbs olefins and is therefore suitable only for the purification of nitrogen, noble gases and saturated hydrocarbons. WO 01/007 383 A1 teaches a method of purifying olefin streams by passing them over porous adsorbents such as carbon black or aluminum oxide and/or silicon oxides. JP 02 144 125 A2 (CAS Abstract 113:177 506) teaches a method of removing carbon monoxide and metal carbonyls from off-gases formed in semiconductor manufacture by adsorption on adsorption compositions comprising manganese oxide and copper oxide. JP 05 337 363 A2 (CAS Abstract 120:274 461) discloses adsorbents for the removal of carbon monoxide which comprise palladium and further oxides on a support, with the oxides being selected from among the oxides of the elements of groups 11, 2 and 12 (without Be, Cd, Hg and Ra), 13 (without Al, Tl and the actinides), 14 (without C, Si, Pb and Hf), 5 and 15 (without N, P, As and the "Pa series"), 6 and 16 (without O, S, Se and U), 7 and 8 of the Periodic Table of the Elements.

WO 95/021 146 A1 teaches a method of removing carbon monoxide and, if present, also arsine from liquid hydrocarbon streams by bringing them into contact with a sorbent which comprises, depending on the embodiment, disperse copper in the oxidation states 0, +1 or +2 and in particular cases also manganese dioxide. EP 537 628 A1 discloses a method of removing carbon monoxide from alpha-olefins and saturated hydrocarbons by bringing them into contact with a catalyst system based on at least one oxide of a metal selected from among Cu, Fe, Ni, Co, Pt and Pd and at least one oxide of a metal selected from groups 5, 6 or 7 of the Periodic Table of the Elements at from 0 to 150° C. U.S. Pat. No. 4,713,090 describes an adsorbent for recovering high-purity carbon monoxide by pressure swing adsorption or temperature swing adsorption. The adsorbent comprises a combination support having a core of silicon oxide or aluminum oxide and an outer layer of an activated carbon on which a copper compound is supported.

WO 2004/022 223 A2 teaches an adsorption composition comprising copper, zinc, zirconium and if desired aluminum and its use in the fully reduced state for removing CO from streams.

Copper-comprising catalysts are also known for applications other than the removal of CO from inert gases or hydrocarbons. U.S. Pat. Nos. 4,593,148 and 4,871,710 disclose Cu/Zn catalysts for removal of sulfur and of arsenic. WO 95/023 644 A1 teaches a copper catalyst for the hydrogenation of carbon oxides, for example to form methanol, or for the shift reaction of carbon monoxide with water to form carbon dioxide and hydrogen, which catalyst comprises disperse copper and also stabilizers such as silicon dioxide, aluminum oxide, chromium oxide, magnesium oxide and/or zinc oxide and if desired also a support such as aluminum oxide, zirconium dioxide, magnesium oxide and/or silicon dioxide, and its activation and passivation. DE 198 48 595 A1 discloses a catalyst for decomposing nitrous oxide which has the general formula $M_xAl_2O_4$ in which M is Cu or a mixture of Cu and Zn and/or Mg and which may comprise further dopants, in particular Zr and/or La. U.S. Pat. No. 5,328,672 teaches an automobile exhaust purification catalyst which comprises an oxide comprising a transition metal and a zeolite comprising a transition metal, with the transition metal being selected from among Cu, Co, Ni, Cr, Fe, Mn, Ag, Zn, Ca and "compatible mixtures thereof" and preferably being identical in oxide and zeolite and particularly preferably being Cu and the oxide being selected from among La oxide, Ti oxide, Si oxide, Zr oxide and preferably being $ZrO_2$. EP 804 959 A1 discloses an $NO_x$ decomposition catalyst which in addition to copper and an MFI zeolite may further comprise $SiO_2$, $Al_2O_3$, $SiO_2/Al_2O_3$, MgO, $ZrO_2$ and the like and also any desired further elements such as the transition elements Pt, Rh, Cr, Co, Y, Zr, V, Mn, Fe and Zn and also Ga, In, Sn, Pb, P, Sb, Mg and Ba, preferably P. DE 199 50 325 A1 teaches a spinel monolith catalyst for the decomposition of NO, which has the general formula $A_xB_{(1-x)}E_2O_4$, where A is Cu of which up to half can be replaced by Co, Fe, Ni, Mn or Cr; B is at least one element selected from among Zn, Mg, Ca, Zr, Ce, Sn, Ti, V, Mo and W and E is Al of which up to half can be replaced by Fe, Cr, Ga, La or a mixture thereof. U.S. Pat. No. 4,552,861 teaches a process for producing catalysts which comprise Cu, Zn, Al and at least one element from the group consisting of the rare earths and zirconium and also their use for the synthesis of methanol. The methanol catalysts disclosed in U.S. Pat. No. 4,780,481 comprise Cu, Zn and at least one alkali metal or alkaline earth metal, noble metals and/or rare earths, with Zn being able to be partly replaced by Zr. WO 96/014 280 A1 teaches catalysts which comprise Cu, Zn and at least one compound of Al, Zr, Mg, a rare earth metal and/or mixtures thereof and their use for the hydrogenation of carboxylic esters. EP 434 062 A1 likewise teaches a process for the hydrogenation of carboxylic esters over a catalyst comprising Cu, Al and a metal selected from the group consisting of Mg, Zn, Ti, Zr, Sn, Ni, Co and mixtures thereof. U.S. Pat. No. 4,835,132 describes CO shift catalysts which are produced by calcination of a precursor of the formula $(Cu+Zn)_6Al_xR_y(CO_3)_{(x+y)/2}OH_{12+2(x+y)} \cdot nH_2O$ having a layer structure, where R is La, Ce or Zr, x is at least 1 and not more than 4, y is at least 0.01 and not more than 1.5 and n is approximately 4.

Methods of activating or reactivating catalysts, including copper-comprising catalysts, or passivating them for transport are also known. DD 0 153 761 relates to a method of activating or reactivating iron molybdate redox catalysts which may also comprise copper, in which the catalysts are firstly calcined in a nonoxidizing atmosphere and are then brought into contact with an oxidizing gas. DE 199 63 441 A1 teaches a method of regenerating copper-comprising hydrogenation catalysts by firstly an oxidizing treatment and then a reducing treatment, with the reduction preferably being carried out only in the hydrogenation reactor. WO 02/068 119 A1 discloses copper-comprising hydrogenation and dehydrogenation catalysts which are used in the reduced state and are passivated for transport by partial oxidation of the copper. EP 296 734 A1 describes copper-comprising shift or methanol catalysts which have a Cu surface area of at least 70 $m^2/g$, based on copper, as a result of reduction at a temperature below 250° C. Such activation, regeneration and passivation methods are also known for other catalysts; for instance, JP 55/003 856 A (WPI-Abstract No. WP198013664C) discloses a method of activating catalysts based on palladium by reduction by means of methanol, oxidation by means of oxygen, then by means of acetic acid and oxygen and final reduction by means of hydrogen. WO 03/002 252 A1 describes an activation method for a cobalt-comprising catalyst by treatment with hydrocarbon.

However, the increasing demands being made of the purity of streams for some applications make new and improved auxiliaries and methods of removing impurities necessary. The removal of carbon monoxide from hydrocarbons, in particular from hydrocarbons which are typically present in liquid form, e.g. propene, 1- or 2-butene, is particularly problematical. It is therefore an object of the invention to find an improved adsorbent and an improved method of removing carbon monoxide from streams by adsorption.

We have accordingly found an adsorption composition comprising copper and zirconium oxides but no zinc oxide, which comprises from 30 to 99.8% by weight of copper oxide and from 0.2 to 70% by weight of zirconium oxide, based on the total amount of the adsorption composition. Furthermore, we have found a method of removing carbon monoxide from streams, in which the adsorption composition of the invention is used as adsorption composition or alternatively the adsorption composition of the invention is used as catalyst for the reaction of carbon monoxide with oxygen or as a reactant with carbon monoxide. In particular, we have found a method of removing carbon monoxide from streams by adsorption, in which the stream comprising carbon monoxide is brought into contact with an adsorption composition which comprises from 30 to 99.8% by weight of copper oxide and from 0.2 to 70% by weight of zirconium oxide, based on the total amount of the adsorption composition.

The adsorption composition of the invention is well suited for use in processes for purifying streams, in particular for removing carbon monoxide (CO) from liquid hydrocarbon streams such as propylene. A particular advantage of the adsorption composition of the invention is its ability to be regenerated readily. Although the adsorption composition of the invention does not have the maximum possible adsorption capacity for CO of such compositions, it can be regenerated considerably better than compositions having a higher CO uptake capacity. It is therefore very suitable for freeing even streams having a highly fluctuating CO content of CO in plants having two adsorbers of which one is being used for adsorption and one is being regenerated.

In the adsorptive method of the invention, the adsorption composition of the invention acts by adsorption. For the purposes of the present invention, adsorption is the attachment of an adsorbate to the surface of an adsorption composition ("adsorbent"), which can generally be reversed by desorption. The adsorbate can also be reacted chemically on the adsorbent; if the adsorbent remains essentially unchanged chemically, the process is referred to as catalysis (example: the known method of reacting CO with oxygen over a metallic copper catalyst to form carbon dioxide), while if the adsorbate reacts chemically with the adsorbent, the process is referred to as absorption (examples: the known method of removing oxygen from gas streams by bringing them into contact with metallic copper to form copper(I) oxide and/or copper(II) oxide and the known method of removing carbon monoxide from gas streams by bringing them into contact with copper(I) oxide and/or copper(I) oxide to form carbon dioxide and metallic copper). In the case of a pure adsorption as in catalysis, the adsorbate or its reaction product is removed again from the surface by desorption, while in the case of absorption a chemical regeneration of the absorbent is usually necessary. Both in the case of catalysis and in the case of absorption, the initial step is in each case an adsorption and whether an adsorptive purification process (e.g. in the regeneration of the adsorption composition) ultimately ends in a catalytic or absorptive step or a purely adsorptive process is present depends on the individual case. For the purposes of the present invention, "adsorptive" means that no reduction product of carbon monoxide is released into the stream during the removal of CO from the stream to be purified and the adsorption composition used remains essentially unchanged chemically, i.e. its composition does not change or changes only insignificantly. On the other hand, whether carbon monoxide or a reaction production thereof is released during regeneration of the adsorbent of the invention, i.e. whether or not catalysis takes place, is of no consequence for the purposes of the invention.

Adsorption compositions or absorption compositions are in everyday speech often also referred to as "catalysts" without actually having a catalytic action in their intended use.

The adsorption composition of the invention comprises copper and zirconium oxides. Copper can also be present entirely or partly as metallic copper and is otherwise in the form of Cu(I) and Cu(II) oxides. Copper is preferably present partly in metallic form and partly in the form of Cu(I) and Cu(II) oxides, i.e. the adsorption composition is "partially reduced" (or "partially oxidized", depending on the way in which it is looked at). The adsorption composition of the invention generally comprises copper in an amount which, calculated as CuO, corresponds to at least 30% by weight, preferably at least 50% by weight and particularly preferably at least 70% by weight and generally not more than 99.8% by weight, preferably not more than 95% by weight and particularly preferably not more than 90% by weight, of copper oxide CuO, in each case based on the total amount of the adsorption composition. Furthermore, the adsorption composition of the invention generally comprises zirconium dioxide $ZrO_2$ in an amount of at least 0.2% by weight, preferably at least 5% by weight and particularly preferably at least 10% by weight, and generally not more than 70% by weight, preferably not more than 50% by weight and particularly preferably not more than 30% by weight, in each case based on the total amount of the adsorption composition.

The percentages of the components of the adsorption composition always add up to 100% by weight.

The adsorption composition comprises, with the exception of unavoidable impurities, no zinc oxide (ZnO).

The adsorption composition preferably consists essentially of copper (oxide) and zirconium dioxide, i.e. apart from copper (oxide) and zirconium oxide, the adsorption composition comprises no further constituents with the exception of insignificant constituents which can, for example, be introduced from manufacture, e.g. residues of starting materials and reagents, auxiliaries for shaping and the like.

A very suitable adsorption composition consists essentially of, for example, about 80% by weight of CuO and about 20% by weight of $ZrO_2$. Another, likewise very suitable adsorption composition consists in pure form of, for example, about 85% by weight of CuO and about 15% by weight of $ZrO_2$.

The adsorption composition of the invention can but does not necessarily have to be present in pure form. It is possible to mix it with auxiliaries or to apply it to an inert support. Suitable inert supports are the known catalyst supports such as aluminum oxide, silicon dioxide, zirconium dioxide, aluminosilicates, clays, zeolites, kieselguhr and the like.

The adsorption composition of the invention is produced like known oxidic catalysts. A convenient and preferred process for producing the adsorption composition of the invention comprises the following process steps in the indicated order:

a) preparation of a solution of the components of the adsorption composition and/or of soluble starting compounds thereof;
b) precipitation of a solid from this solution by addition of a base;
c) isolation and drying of the solid;
d) if desired calcination of the solid;
e) shaping of the solid to give shaped bodies; and
f) if desired calcination of the shaped bodies;

with the proviso that at least one of the two calcinations steps d) or f) is carried out.

In the first process step, step a), a solution of the components of the adsorption composition is prepared in a customary way, for example by dissolution in an acid such as nitric acid. If desired, starting compounds of the components of the adsorption composition, for example the nitrates, carbonates, hydroxycarbonates of the metals dissolved in an aqueous solution which may be acidic, for example acidified with nitric acid, are used instead of the components themselves. The ratio of the salts in the solution is calculated and set according to the stoichiometry of the desired final composition of the adsorption composition.

A solid is precipitated as precursor of the adsorption composition from this solution in step b). This is carried out in a customary way, for example by increasing the pH of the solution by addition of a base, for instance by addition of sodium hydroxide solution or sodium carbonate solution.

The solid precipitation product formed is generally separated off from the supernatant solution, for instance by filtration or decantation, and washed with water to free it of soluble constituents such as sodium nitrate before drying in step c). The precipitation product is then normally dried by means of customary drying methods before further processing. In general, treatment at slightly elevated temperature, for instance at least 80° C., preferably at least 100° C. and particularly preferably at least 120° C., for a period of from 10 minutes to 12 hours, preferably from 20 minutes to 6 hours and particularly preferably from 30 minutes to 2 hours, is sufficient for this. It is also possible and particularly convenient to convert the product of the precipitation directly (a certain alkali metal, for example sodium, content of the adsorption composition generally does not interfere) or after washing into a dry further-processable powder by spray drying.

After drying, the precipitated and dried precursor of the adsorption composition is, if desired, subjected to the calcination step d). The calcination temperature employed is generally at least 200° C., preferably at least 250° C. and particularly preferably at least 270° C., and generally not more than 500° C., preferably not more than 450° C. and particularly preferably not more than 410° C. The calcination time is generally at least 10 minutes, preferably at least 20 minutes and particularly preferably at least 30 minutes, and generally not more than 12 hours, preferably not more 6 hours and particularly preferably not more than 4 hours. The drying step c) and the calcination step d) can go over directly into one another.

After the drying step c) or the calcination step d), the adsorption composition or its precursor is processed in the shaping step e) by means of customary shaping methods such as extrusion, tableting or pelletization to give shaped bodies such as extrudates, tablets or pellets, including spherical pellets.

After the shaping step, the adsorption composition or its precursor is, if desired, subjected to a calcination step f). The calcinations conditions to be employed in step f) are identical to those of the calcination step d).

During the course of its production, the adsorption composition is subjected to at least one of the two calcination steps d) or f), if desired both. In the calcination step or steps, the adsorption composition precursor is converted into the actual adsorption composition and, inter alia, the BET surface area and the pore volume of the adsorption composition are set in a customary manner with the BET surface area and the pore volume decreasing, as is known, with increasing calcination time and calcination temperature.

Preference is given to continuing calcination at least until the BET surface area of the adsorption composition is in the range from at least 40 to not more than 100 $m^2/g$. The pore volume of the adsorption composition, measured as water absorption, is set to a value of at least 0.05 ml/g during the calcination. These values are preferred for the adsorption composition of the invention.

The adsorption composition of the invention can also, as mentioned above, be deposited on a support. This is achieved by means of customary impregnation processes or precipitation deposition processes. A precipitation deposition process is, as is known, a precipitation process in the presence of a support or a support precursor. To carry out a precipitation deposition process, a support or support precursor is preferably added to the solution prepared in step a) in the above-described precipitation process. If the support is present in the form of finished preformed shaped bodies, i.e. in the case of a pure impregnation process, the shaping step e) is omitted; otherwise, the support is formed during the course of processing of the precursor of the adsorption composition by precipitation, drying, calcination and shaping.

A preferred impregnation process for producing the adsorption composition of the invention is carried out using preformed supports and comprises the following process steps in the indicated order:

a) preparation of a solution of the components of the adsorption composition and/or of soluble starting compounds thereof;
b) impregnation of a preformed support with the solution;
c) drying of the impregnated support; and
d) calcination of the impregnated and dried support.

Process step a) of this impregnation process is carried out like the above-described step a) of the precipitation process. In step b), a preformed support is impregnated with the solution. The preformed support has a shaped selected according to the application, for example extrudates, tablets or pellets, including spherical pellets. The impregnation is carried out either using supernatant solution or as an impregnation with the amount of solution corresponding to the pore volume of the support ("incipient wetness"). After the impregnation, the impregnated support is dried and calcined like the precipitation product in the precipitation process in step c) and d). In the case of a preformed support, the shaping step is omitted.

To use the shaped adsorption composition bodies, they are introduced into a vessel usually referred to as an "adsorber" but sometimes also "reactor" in which they are brought into contact with the stream to be purified.

The finished adsorption composition is preferably activated before being used for adsorbing CO. It is also advisable to dry it again to remove traces of adhering moisture and increase the adsorption capacity before it is used.

This renewed drying and the activation are conveniently carried out in the adsorber since otherwise great efforts have to be made to protect the ready-to-use activated adsorption composition from air and moisture while introducing it into the adsorber.

The renewed drying of the precursor of the adsorption composition, if necessary, is achieved by heating the precursor to a temperature of generally at least 100° C., preferably at least 150° C. and particularly preferably at least 180° C., and generally not more than 300° C., preferably not more than 250° C. and particularly preferably not more than 220° C. A suitable drying temperature is, for example, about 200° C. The precursor is maintained at the drying temperature until only residues of adhering moisture which no longer interfere are present; this is generally the case after a drying time of at least 10 minutes, preferably at least 30 minutes and particularly preferably at least 1 hour, and generally not more than 100 hours, preferably not more than 10 hours and particularly preferably not more than 4 hours. Drying preferably takes place in a gas stream in order to transport the moisture out of the bed. It is possible, for example, to use dry air for this purpose, but particular preference is given to passing an inert gas, in particular nitrogen or argon, through the bed.

The activation is effected by at least partial reduction of the copper comprised in the adsorption composition to copper metal or copper(I) compounds. This can in principle be carried out using any reducing agent which is able to reduce copper from the oxidation states I or II to the oxidation state 0. This can be effected by means of liquid or dissolved reducing agents; in this case, drying has to be carried out after the activation. For this reason, reduction using a gaseous reducing agent after drying, especially reduction by means of hydrogen by passing a hydrogen-comprising gas over the precursor, is very much more convenient. The temperature to be employed in the activation is generally at least 80° C., preferably at least 100° C. and particularly preferably at least 110° C., and generally not more than 20° C., preferably not more than 160° C. and particularly preferably not more than 130° C. A suitable activation temperature is, for example, about 120° C. The reduction is exothermic. The amount of reducing agent should be set so that the temperature does not go outside the chosen temperature window. The course of the activation can be monitored with the aid of the temperature measured in the bed of the adsorbent ("temperature-programmed reduction, TPR").

A preferred method of activating the adsorption composition is to set the desired activation temperature after a drying step carried out under a stream of inert gas and to mix a small amount of hydrogen into the stream of inert gas.

An inert gas is any gas or gas mixture which is inert under the conditions, for example nitrogen, helium, neon, krypton, xenon, argon or a mixture thereof. Preference is given to using nitrogen.

A gas mixture suitable for the activation initially comprises, for example, at least 0.1% by volume of hydrogen in nitrogen, preferably at least 0.5% by volume and particularly preferably at least 1% by volume, and not more than 10% by volume, preferably not more than 8% by volume and particularly preferably not more than 5% by volume. A suitable value is, for example, 2% by volume. This initial concentration is either maintained or increased in order to attain and maintain the desired temperature window.

The reduction is complete when, despite a constant or increasing level of the reducing agent, the temperature in the bed of the adsorption composition decreases. The copper comprised in the adsorption composition is preferably not completely reduced to metallic copper, so that the activated adsorption composition comprises both metallic copper and oxidic copper. A typical activation time in this case is generally at least 1 hour, preferably at least 10 hours and particularly preferably at least 15 hours, and generally not more than 100 hours, preferably not more than 50 hours and particularly preferably not more than 30 hours.

Should the proportion of metallic copper become too high, the adsorption composition can also be oxidized in an analogous manner. For this purpose, preference is given to passing an oxygen/inert gas mixture rather than a hydrogen/inert gas mixture over the adsorption composition. As an alternative, the activation can also be deliberately effected by complete reduction of the adsorption composition with subsequent reoxidation to a desired degree of oxidation. A suitable method is, for example, reduction at 200° C. in a stream of hydrogen or hydrogen/inert gas with subsequent reoxidation at room temperature by means of a stream of oxygen/inert gas. Such methods are known for copper-comprising catalysts.

After the activation, the adsorption composition of the invention is ready for operation.

The adsorptive method of the invention is a method of removing carbon monoxide from streams by adsorption, in which the stream comprising carbon monoxide is brought into contact with an adsorption composition which comprises copper and zirconium oxides. The adsorptive method of the invention is thus distinguished by the use of the adsorption composition of the invention. An advantage of the adsorptive method of the invention is its applicability to streams which are either free of oxygen and are at a temperature which is insufficient for the conventional catalytic reaction of carbon monoxide with oxygen to form carbon dioxide or in whose further use carbon dioxide or oxygenates interfere.

In principle, any stream, for example inert gas streams (nitrogen, helium, neon, krypton, xenon and/or argon) or hydrocarbon streams such as alkanes (methane, ethane, propane, butane, mixtures thereof, isomers and isomer mixtures) or alkenes (also known as "olefins") such as ethene, propene, 1-butene, 2-butene, 1,3-butadiene and/or styrene, can be freed of contamination by carbon monoxide by means of the adsorptive method of the invention.

It is likewise possible to use the adsorption composition of the invention in a nonadsorptive manner to remove carbon monoxide. This is particularly advantageous when the stream to be freed of carbon monoxide comprises not only carbon monoxide but also oxygen and is at a temperature which is sufficiently high for the catalytic reaction of oxygen with carbon monoxide and in whose further use carbon dioxide or oxygenates do not interfere. Thus, carbon monoxide in streams comprising carbon monoxide and oxygen can be reacted by catalytic reaction with oxygen over the adsorption composition of the invention used as catalyst to form carbon dioxide and thus be removed from the stream. Likewise, carbon monoxide can be removed from streams comprising carbon monoxide by reaction of carbon monoxide with an adsorption composition according to the invention comprising copper(I) oxide and/or copper(II) oxide to form metallic copper and carbon dioxide. It is equally possible to removed oxygen from streams by adsorption on the adsorption composition of the invention comprising metallic copper with formation of copper(I) oxide and/or copper(II) oxide, or in the presence of hydrogen by copper-catalyzed formation of water. As in the case of other copper-comprising compositions, not only carbon monoxide, oxygen and together with the latter also hydrogen, but also other contaminants which react with copper or copper oxide, for example elemental mercury and/or mercury-, sulfur-, antimony- and/or arsenic-comprising compounds, can be removed from streams by means of the adsorption composition of the invention. In other words: the adsorption composition of the invention can be used in all known processes in which copper-comprising solids are used catalytically, absorptively or as reactants.

The adsorptive method of the invention is preferably used for removing carbon monoxide from alkene streams, in particular for removing carbon monoxide from alkene streams which are usually in liquid form. Alkenes in liquid form typically do not have, except when unusually high pressures are employed, the temperature necessary for the catalytic removal of carbon monoxide by reaction with oxygen, and in addition the oxygenate formation would interfere in the subsequent use for polymerization.

The adsorptive method of the invention is particularly useful for removing carbon monoxide from propene, 1-butene, 2-butene, 1,3-butadiene, butene mixtures, butene/butadiene mixtures or styrene in order to reduce the carbon monoxide content to the values permissible for "polymer grade" olefins. In a very particularly preferred embodiment, carbon monoxide is removed adsorptively from liquid propene by means of the method of the invention.

The adsorptive method of the invention makes it possible to remove carbon monoxide from streams. It is particularly useful for removing carbon monoxide from streams which generally comprise at least 0.001 ppm (ppm by volume in the case of gases, ppm by weight in the case of liquids), preferably at least 0.01 ppm, and generally not more than 1000 ppm, preferably not more than 100 ppm and particularly preferably not more than 10 ppm, of carbon monoxide. In the case of relatively high initial concentrations of carbon monoxide, it is usually more economical to carry out another known purification methods such as distillation, catalytic oxidation of the carbon monoxide by means of oxygen to form carbon dioxide or oxidation of the carbon monoxide by means of copper oxide to form metallic copper and carbon dioxide, if desired with subsequent removal of carbon dioxide and oxygenates, beforehand since otherwise the adsorption capacity of the adsorption composition can be reached too quickly.

To carry out the adsorptive method of the invention, the stream to be freed of carbon monoxide is passed over the bed of the shaped bodies of the adsorption composition of the invention in the adsorber.

The temperature for the adsorptive method of the invention is not critical or relatively noncritical from a technical point of view. Typical temperatures are in the range of at least −270° C., preferably at least −100° C. and particularly preferably −40° C., and not more than 300° C., preferably not more than 200° C. and particularly preferably not more than 100° C. The temperature is conveniently not influenced separately but the method of the invention is instead carried out at the temperature of the stream to be treated.

The important parameter which determines the degree of depletion is, apart from the temperature which is, as described, conveniently not influenced separately, the contact time between stream and adsorption composition. This contact time is determined by the flow rate of the stream and the volume of the bed of adsorption composition. The volume flow of the stream to be purified will usually be determined by the capacity of parts located upstream or downstream. Furthermore, the adsorption capacity of the adsorption composition is limited, so that a particular amount of adsorption composition can be utilized for the method of the invention for a particular time before it has to be regenerated. Although this makes the use of a very large amount of adsorption composition desirable, the costs which increase with the size of the adsorber stand in the way of this. The amount of adsorption composition in the adsorber is therefore selected in the individual case so that firstly the desired degree of depletion and secondly a tolerably short operating time of an adsorber between two regenerations of the adsorption composition are achieved. It is advantageous to provide at least two adsorbers of which at least one can be supplied with the stream to be purified while the adsorption composition in at least one other is regenerated. This is a routine optimization exercise for a person skilled in the art.

Depending on the adsorber size selected, the maximum uptake capacity of the adsorption composition present therein for carbon monoxide so that it has to be regenerated is reached sooner or later.

To regenerate the adsorption composition of the invention, the stream to be purified is firstly stopped; it is preferably fed into a parallel adsorber filled with fresh or regenerated adsorption composition.

The adsorption composition to be regenerated is subsequently regenerated. This occurs by desorption. Here, it is immaterial whether the adsorbed carbon monoxide reacts catalytically with any adsorbed oxygen or purely chemically by reaction with copper oxide present in the adsorption composition to form carbon dioxide or in another way, for instance with any hydrogen present to form methanol or methane, prior to the desorption and these reaction products are subsequently desorbed; the important thing is the reestablishment of the adsorption capacity of the adsorption composition.

Desorption is carried out by passing a fluid, preferably a gas, over the adsorption composition, by increasing the temperature or by means of a combination of these measures. A preferred procedure is to pass a gas through the adsorber in which the adsorption composition to be regenerated is present and at the same time heating the adsorber. The gas can be inert, for example nitrogen, methane or argon, but it is also possible to use hydrogen in which case the CO is converted into methanol or methane. The desorption temperature is generally set to a value of at least 50° C., preferably at least 100° C. and particularly preferably at least 150° C., and generally not more than 500° C., preferably not more than 450° C. and particularly preferably not more than 400° C. For example, a desorption temperature of about 300° C. is suitable. The duration of the regeneration is typically at least 1 hour, preferably at least 10 hours and particularly preferably at least 15 hours, and generally not more than 100 hours, preferably not more than 50 hours and particularly preferably not more than 30 hours.

To replace oxygen lost from the copper, it is often advantageous to carry out the desorption using an inert gas, preferably nitrogen or argon, comprising traces of oxygen. It is convenient to use nitrogen which generally comprises oxygen in an amount of at least 1 ppm, preferably at least 5 ppm and particularly preferably at least 10 ppm, and generally not more than 300 ppm, preferably not more than 250 ppm and particularly preferably not more than 200 ppm, for desorption.

The actual desorption can also be initiated with the removal of residual stream to be purified from the adsorber by flushing of the adsorber, advantageously at room temperature with the gas stream used for desorption.

After this regeneration, the absorption composition is generally ready for immediate renewed use. In particular cases, especially when the desired degree of reduction has changed too much, it can be advisable or necessary to subject the adsorption composition to renewed setting of the degree of reduction.

The adsorption composition of the invention and the adsorptive method of the invention make it possible to remove carbon monoxide from streams in a simple and economical way. The streams which have been purified in this way can subsequently be employed for their intended use.

EXAMPLES

General Method of Producing the Adsorption Compositions 1200 ml of distilled water are placed in a 10 l reaction vessel and heated to 70° C. After this temperature has been reached, solutions of the metal nitrates are pumped in in the amount necessary to achieve the desired composition while stirring. The pH of the mixture is maintained at 6.5 by simultaneous metering-in of a 20% strength by weight sodium carbonate solution. The suspension formed is stirred further at 70° and pH 6.5 for 120 minutes. The hot suspension is subsequently filtered and the solid is washed with cold distilled water until free of nitrate. The powder is dried, calcined at 300° C. for 4 hours and tableted to produce 3×3 mm pellets. After renewed drying and complete reduction by means of a hydrogen/nitrogen mixture, the adsorption composition is partially oxidized by bringing it into contact with a mixture of 0.6% by volume of oxygen in nitrogen for one hour at room temperature.

The adsorption compositions indicated in the table were obtained by this general method.

General Method for Determining the CO Adsorption Capacity

A gas mixture of 100 ppm of CO in propylene is passed at a GHSV of 1765 h$^{-1}$ (corresponding to 150 standard l of propylene/h) over 85 ml of the adsorption composition at room temperature and ambient pressure (i.e. only the pressure necessary for flow through the bed is applied upstream of the reactor) in a tube reactor (adsorber). The CO concentration in the offgas is measured continuously. The 10%, 20% and 50% "breakthrough points", i.e. in each case the ratio of the volume of CO (calculated as pure substance) fed to the adsorption composition to the volume of the adsorption composition at which 10%, 20% or 50% of the CO concentration of the gas mixture fed to the adsorber is measured after passage through the adsorber, are reported. These breakthrough points are accordingly a measure of the adsorption capacity of the adsorption composition.

The breakthrough points reported in the table were measured by this general method.

| Example No. | Composition [% by weight] | | | Breakthrough points [l of CO/l of adsorption composition] | | |
|---|---|---|---|---|---|---|
| | CuO | ZrO$_2$ | ZnO | 10 | 20 | 50 |
| 1 (comparison) | 50 | 10 | 40 | 1.73 | 2.14 | n.d. |
| 2 (comparison) | 60 | 10 | 30 | 2.14 | 2.61 | 6.02 |
| 3 (comparison) | 60 | 20 | 20 | 1.6 | 2.19 | 4.18 |
| 4 (comparison) | 70 | 10 | 20 | 2.56 | 3.19 | 7.16 |
| 5 (comparison) | 70 | 20 | 10 | 1.52 | 2.12 | 6.32 |
| 6 (comparison) | 80 | 0 | 20 | 1.35 | 1.73 | 3.61 |
| 7 (comparison) | 80 | 10 | 10 | 2.62 | 3.28 | n.d. |
| 8 (comparison) | 100 | 0 | 0 | 0.05 | 0.06 | 0.1 |
| 9 | 62 | 38 | 0 | 3.91 | n.d. | n.d. |
| 10 | 75 | 25 | 0 | 4.82 | 5.63 | 8.06 |
| 11 | 80 | 20 | 0 | 4.71 | 5.36 | 6.74 |
| 12 | 82 | 18 | 0 | 5.07 | 6.39 | 10.5 |
| 13 | 85 | 15 | 0 | 5.96 | 7.49 | >9.95 |
| 14 | 87 | 13 | 0 | n.d. | n.d. | n.d. |
| 15 | 90 | 10 | 0 | 4.39 | 6.39 | 12.1 |
| 16 | 95 | 5 | 0 | 1.79 | 2.67 | n.d. |

The examples and comparative examples show that the uptake capacity of the adsorption composition of the invention is higher than that of a known adsorption composition which further comprises zinc oxide.

The invention claimed is:

1. A method of removing carbon monoxide from hydrocarbon streams comprising carbon monoxide by adsorption on an adsorption composition, wherein the hydrocarbon streams comprising carbon monoxide is brought into contact with an adsorption composition comprising copper and zirconium oxides but no zinc oxide, which comprises from 30 to 99.8% by weight of copper oxide and from 0.2 to 70% by weight of zirconium oxide, based on the total amount of the adsorption composition.

2. The method according to claim 1, wherein carbon monoxide is removed from the hydrocarbon streams comprising liquid propylene.

3. A method of removing carbon monoxide from hydrocarbon streams comprising carbon monoxide by adsorption on an adsorption composition, wherein the stream comprising carbon monoxide is brought into contact with an adsorption composition consisting essentially of from 30 to 99.8% by weight of copper oxide and from 0.2 to 70% by weight of zirconium oxide.

4. A method of removing carbon monoxide from hydrocarbon streams comprising carbon monoxide by adsorption on an adsorption composition, wherein the stream comprising carbon monoxide is brought into contact with an adsorption composition consisting of from 30 to 99.8% by weight of copper oxide and from 0.2 to 70% by weight of zirconium oxide.

5. A method of removing carbon monoxide from hydrocarbon streams comprising carbon monoxide by adsorption on an adsorption composition, wherein the hydrocarbon streams comprising carbon monoxide is brought into contact with an adsorption composition comprising copper and zirconium oxides but no zinc oxide, which comprises from 30 to 99.8% by weight of copper oxide and from 0.2 to 70% by weight of zirconium oxide, based on the total amount of the adsorption composition wherein the adsorption composition is deposited on an insert support.

* * * * *